United States Patent
Park et al.

(10) Patent No.: US 9,101,324 B2
(45) Date of Patent: Aug. 11, 2015

(54) VITAL SIGN MEASUREMENT ROBOT AND CONTROL METHOD THEREOF

(75) Inventors: Heum Yong Park, Suwon-si (KR); Yong Jae Kim, Seoul (KR); Youn Baek Lee, Suwon-si (KR); Jeong Hun Kim, Suwon-si (KR); Kyung Shik Roh, Seongnam-si (KR); Young Do Kwon, Yongin-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 704 days.

(21) Appl. No.: 13/296,355

(22) Filed: Nov. 15, 2011

(65) Prior Publication Data
US 2012/0143028 A1 Jun. 7, 2012

(30) Foreign Application Priority Data
Dec. 3, 2010 (KR) ........................ 10-2010-0123003

(51) Int. Cl.
*A61B 5/04* (2006.01)
*A61B 5/00* (2006.01)

(52) U.S. Cl.
CPC ................. *A61B 5/4887* (2013.01); *A61B 5/04* (2013.01); *A61B 5/6835* (2013.01); *A61B 5/6843* (2013.01); *A61B 5/6844* (2013.01); *A61B 5/6887* (2013.01)

(58) Field of Classification Search
CPC ...... A61B 5/04; A61B 5/0402; A61B 5/0408; A61B 5/04085; A61B 5/0478; A61B 5/0492; A61B 5/053; A61B 5/0531; A61B 5/0533; A61B 5/4869; A61B 5/6835; A61B 5/6843; A61B 5/6844; A61B 2560/0462; A61B 2560/0468; A61B 2562/16

USPC ......... 600/372, 382, 384, 386, 393, 509, 301, 600/544
See application file for complete search history.

(56) References Cited

U.S. PATENT DOCUMENTS 5,546,942 A * 8/1996 Zhang ............................ 600/427
8,244,402 B2 * 8/2012 Wells et al. .................... 700/250

(Continued)

FOREIGN PATENT DOCUMENTS

| KR | 10-2009-0034647 | 4/2009 |
| KR | 10-2010-0025446 | 9/2010 |

OTHER PUBLICATIONS

Bajd et al. "Robotics, Intelligent Systems, Control and Automation: Science and Engineering 43" Ch. 5, Robot Sensors, pp. 49-65 Springer (2010).*

*Primary Examiner* — Lee S Cohen
*Assistant Examiner* — Erin M Cardinal
(74) *Attorney, Agent, or Firm* — Harness, Dickey & Pierce, P.L.C.

(57) ABSTRACT

A vital sign measurement robot which automatically measures vital signs, and a control method thereof. The vital sign measurement robot includes an input unit to receive vital sign measurement instructions, an image recognition unit to detect a distance between the robot and a person, vital signs of whom are to be measured, and a measurement portion of the body of the person, when the vital sign measurement instructions are received, a control unit to move electrodes provided on hands so as to locate the electrodes at the measurement portion of the body of the person, when the distance between the robot and the person and the measurement portion of the body of the person are detected, and a vital sign measurement unit to measure a vital sign, when the electrodes are located at the measurement portion of the body of the person.

7 Claims, 9 Drawing Sheets

(56) References Cited

U.S. PATENT DOCUMENTS

| | | | |
|---|---|---|---|
| 2004/0008337 A1* | 1/2004 | Boman | 356/139.03 |
| 2006/0020216 A1* | 1/2006 | Oishi et al. | 600/500 |
| 2006/0025701 A1* | 2/2006 | Kasahara | 600/547 |
| 2007/0049848 A1* | 3/2007 | Koblanski | 600/587 |
| 2007/0055152 A1* | 3/2007 | Ukubo et al. | 600/437 |
| 2009/0285664 A1* | 11/2009 | Kim et al. | 414/730 |
| 2010/0022895 A1* | 1/2010 | Kim et al. | 600/485 |
| 2010/0210946 A1* | 8/2010 | Harada et al. | 600/443 |

* cited by examiner

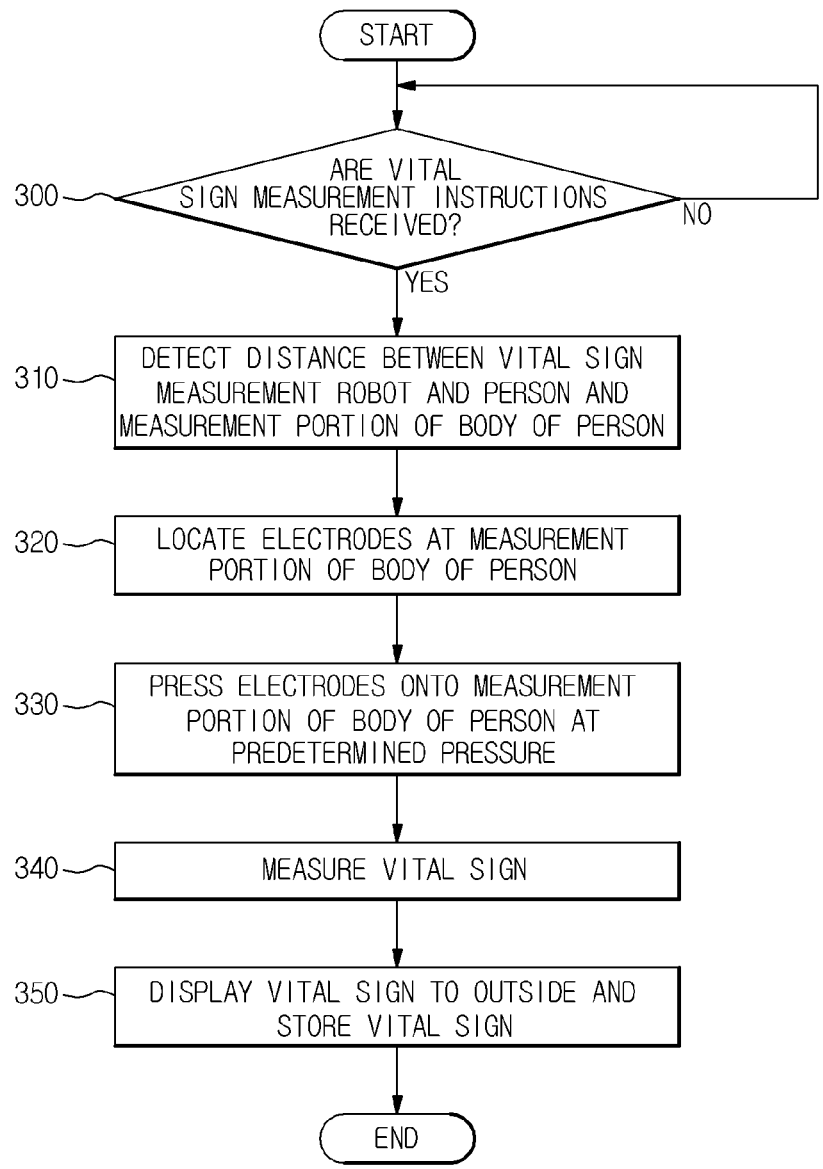

VITAL SIGN MEASUREMENT ROBOT AND CONTROL METHOD THEREOF

CROSS-REFERENCE TO RELATED APPLICATIONS

This application claims the benefit of Korean Patent Application No. 2010-0123003, filed on Dec. 3, 2010 in the Korean Intellectual Property Office, the disclosure of which is incorporated herein by reference.

BACKGROUND

1. Field

Embodiments relate to a vital sign measurement robot which measures vital signs, and a control method thereof.

2. Description of the Related Art

Recently, research and development of intelligent robots which recognize circumstances and achieve autonomous judgment has progressed. Intelligent robots include industrial robots, home service robots, rehabilitation robots, elder assisting robots and construction robots. Application of intelligent robots is being expanded to medicine and biotechnology.

As medical environments change from a supplier-leading type to a customer-leading type, remote medical treatment is increasingly employed. Remote medical treatment has developed into a ubiquitous health care system in which a patient's health is monitored and checked anywhere and anytime through rapid development and supply of telecommunication technology.

In the ubiquitous health care system, it is important for vital signs to be monitored and checked without causing inconvenience to a wearer. In a conventional vital sign measurement method, in order to measure vital signs, electrodes need to be attached to a body of a patient either by a nurse or by the patient, thereby causing inconvenience.

SUMMARY

Therefore, it is an aspect of an embodiment to provide a vital sign measurement robot which automatically measures vital signs, and a control method thereof.

Additional aspects of embodiments will be set forth in part in the description which follows and, in part, will be obvious from the description, or may be learned by practice of the embodiments.

In accordance with an aspect of an embodiment, a vital sign measurement robot includes an input unit to receive vital sign measurement instructions, an image recognition unit to detect a distance between the vital sign measurement robot and a person, vital signs of whom are to be measured, and a measurement portion of the body of the person, when the vital sign measurement instructions are received, a control unit to move electrodes provided on hands so as to locate the electrodes at the measurement portion of the body of the person, when the distance between the vital sign measurement robot and the person, the vital signs of whom are to be measured, and the measurement portion of the body of the person are detected, and a vital sign measurement unit to measure a vital sign, when the electrodes are located at the measurement portion of the body of the person.

At least one hand may be provided, and at least one finger may be provided at each of the at least one hand such that each of the electrodes is attached to each of the at least one finger.

The vital sign measurement robot may further include a database to store measurement portions of the bodies of persons, vital signs of whom are to be measured, according to types of the vital signs, and the image recognition unit may sense a three-dimensional image of the person and sense the measurement portion of the body of the person from the three-dimensional image of the person.

The vital sign measurement robot may further include a pressure sensor to measure pressure applied by the electrodes to the measurement portion of the body of the person, and when the electrodes provided on the hands are located at the measurement portion of the body of the person, the control unit may control the electrodes so as to be pressed onto the measurement portion of the body of the person at a predetermined pressure according to data transferred from the pressure sensor.

When the electrodes provided on the hands are located at the measurement portion of the body of the person, the control unit may control the electrodes so as to be pressed onto the measurement portion of the body of the person at a predetermined pressure through impedance control.

The vital sign measurement robot may further include a tachometer to measure absolute positions of respective joints of the vital sign measurement robot, and the tachometer may sense joint angles of the joints and transfers the joint angles to the control unit and the control unit may calculate absolute coordinates of the respective joints from the joint angles.

The vital sign measurement robot may further include a display unit to display data regarding the vital sign, and when the control unit receives the data regarding the vital sign from the vital sign measurement unit, the control unit may output the data regarding the vital sign through the display unit.

In accordance with another aspect of an embodiment, a control method of a vital sign measurement robot includes detecting a distance between the vital sign measurement robot and a person, vital signs of whom are to be measured, and a measurement portion of the body of the person, when vital sign measurement instructions are received, moving electrodes provided on hands according to data regarding the distance between the vital sign measurement robot and the person, the vital signs of whom are to be measured, and the measurement portion of the body of the person, so as to locate the electrodes at the measurement portion of the body of the person, pressing the electrodes onto the measurement portion of the body of the person at a predetermined pressure, and measuring a vital sign received through the electrodes.

The pressing of the electrodes onto the measurement portion of the body of the person at the predetermined pressure may be achieved by measuring pressure applied by the electrodes to the measurement portion of the body of the person using a pressure sensor and then controlling the pressure.

The pressing of the electrodes onto the measurement portion of the body of the person at the predetermined pressure may be achieved by controlling pressure applied by the electrodes to the measurement portion of the body of the person through impedance control.

The detecting of the measurement portion of the body of the person may be achieved by recognizing a three-dimensional shape of the person and then selecting one of data stored in advance corresponding to the three-dimensional shape of the person.

BRIEF DESCRIPTION OF THE DRAWINGS

These and/or other aspects of embodiments will become apparent and more readily appreciated from the following description of the embodiments, taken in conjunction with the accompanying drawings of which:

FIG. 9 is a flow chart illustrating a control method of a vital sign measurement robot in accordance with an embodiment.

DETAILED DESCRIPTION

Figure 1:
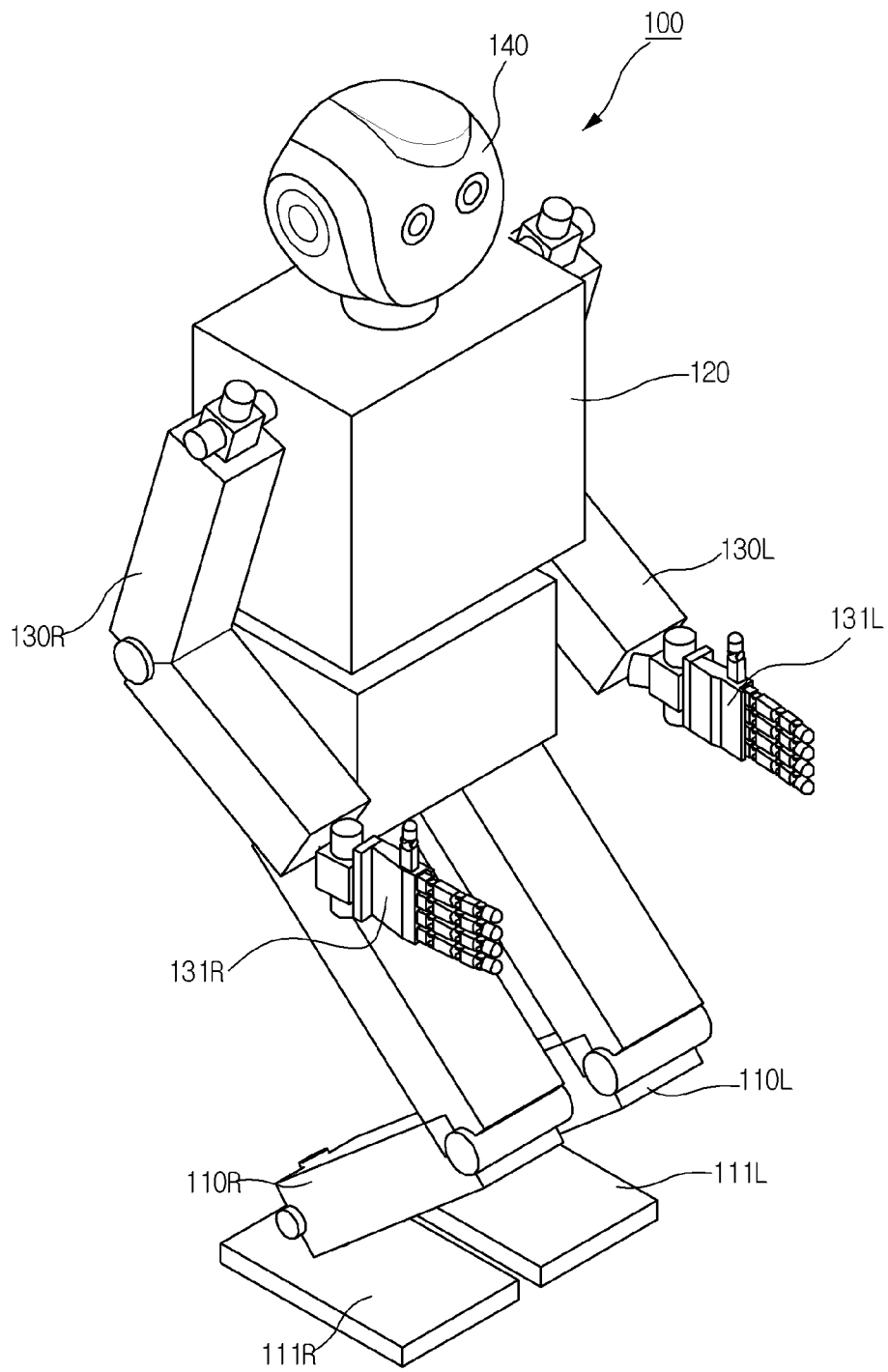
FIG. 1 is a perspective view illustrating the external appearance of a vital sign measurement robot in accordance with an embodiment.

Reference will now be made in detail to embodiments, examples of which are illustrated in the accompanying drawings, wherein like reference numerals refer to like elements throughout.

FIG. 1 is a perspective view illustrating the external appearance of a vital sign measurement robot in accordance with an embodiment.

A vital sign measurement robot 100 in accordance with an embodiment may be any one of various robots, such as a walking robot and a wheel type robot. Hereinafter, a walking robot will be exemplarily described.

The vital sign measurement robot 100 is a bipedal walking robot which walks upright using two legs 110R and 110L in the same manner as a human. The vital sign measurement robot 100 includes a torso 120, two arms 130R and 130L and a head 140 provided at the upper portion of the torso 120, the two legs 110R and 110L provided at the lower portion of the torso 120, hands 131R and 131L respectively provided at the ends of the two arms 130R and 130L, and feet 111R and 111L respectively provided at the ends of the two legs 110R and 110L.

Here, 'R' and 'L' represent right and left sides of the vital sign measurement robot 100, respectively, 'COG (Center of Gravity)' represents a position of the center of gravity of the vital sign measurement robot 100, and 'ZMP' represents a point at which the sum total of a moment in the roll direction (i.e., in the x-axis direction denoting a direction of walking of the vital sign measurement robot) and a moment in the pitch direction (i.e., in the y-axis direction denoting a direction of strides of the vital sign measurement robot) on a contact surface with the ground becomes zero.

Figure 2:
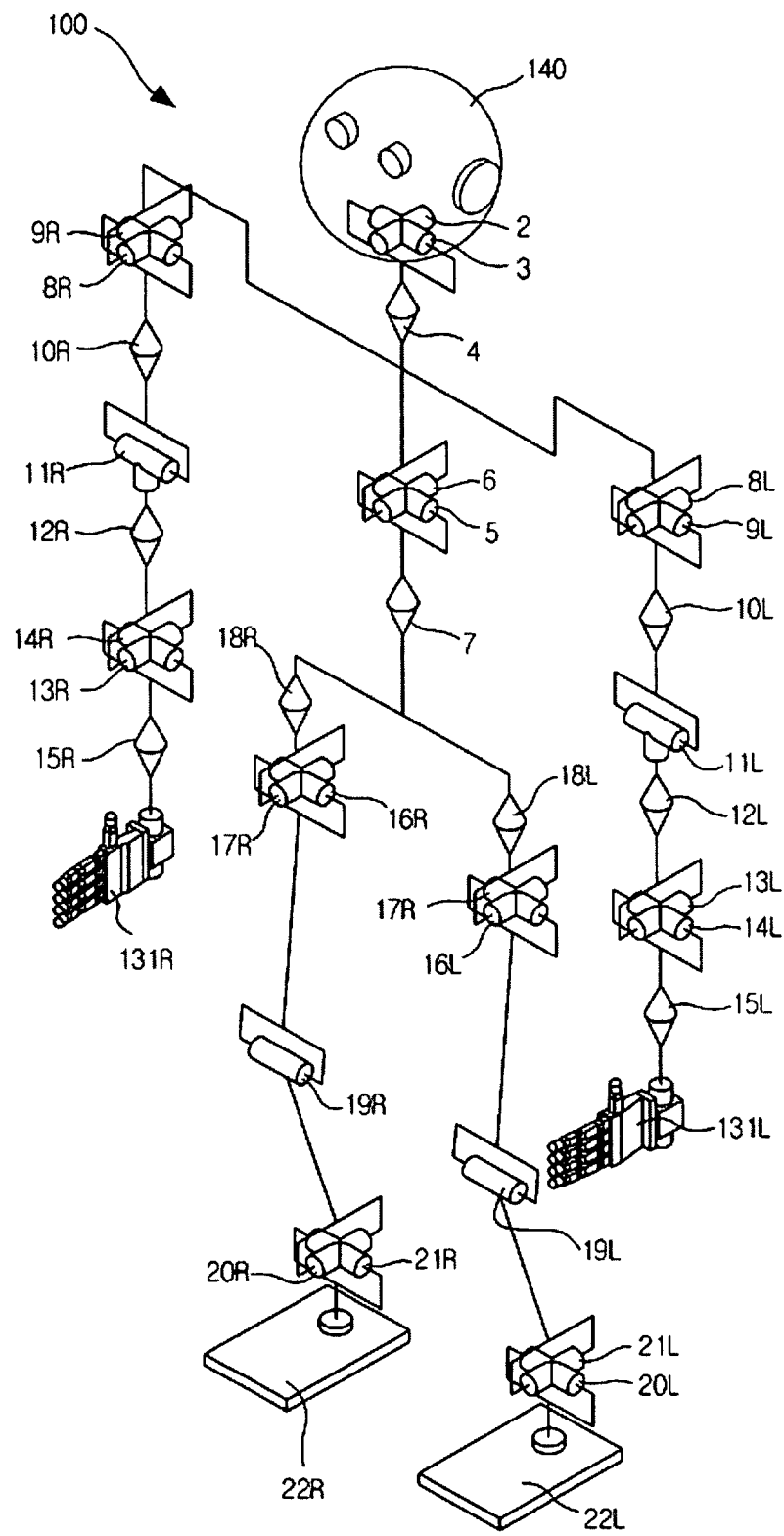
FIG. 2 is a view illustrating structures of main joints of the vital sign measurement robot in accordance with an embodiment.

FIG. 2 is a view illustrating structures of main joints of the vital sign measurement robot in accordance with an embodiment.

A neck joint unit to support the head 140 includes a rotary joint 2 in the roll direction, a rotary joint 3 in the pitch direction, and a rotary joint 4 in the yaw direction, thereby being rotated in the x-axis direction (in the roll direction), in the y-axis direction (in the pitch direction), and in the z-axis direction (in the yaw direction). The two arms 130R and 130L respectively include shoulder joint units, elbow joint units and wrist joint units so that parts of the vital sign measurement robot 100 corresponding to shoulders, elbows and wrists are rotatable.

The shoulder joint units of the two arms 130R and 130L respectively include rotary joints 8R and 8L in the roll direction, rotary joints 9R and 9L in the pitch direction, and rotary joints 10R and 10L in the yaw direction, thereby being rotatable in the x-axis direction (in the roll direction), in the y-axis direction (in the pitch direction), and in the z-axis direction (in the yaw direction).

The elbow joint units of the two arms 130R and 130L respectively include rotary joints 11R and 11L in the pitch direction and rotary joints 12R and 12L in the yaw direction, thereby being rotatable in the y-axis direction (in the pitch direction) and in the z-axis direction (in the yaw direction).

The wrist joint units of the two arms 130R and 130L respectively include rotary joints 13R and 13L in the roll direction, rotary joints 14R and 14L in the pitch direction, and rotary joints 15R and 15L in the yaw direction, thereby being rotatable in the x-axis direction (in the roll direction), in the y-axis direction (in the pitch direction), and in the z-axis direction (in the yaw direction).

The torso 120 includes a rotary joint 5 in the roll direction, a rotary joint 6 in the pitch direction and a rotary joint 7 in the yaw direction, thereby being rotatable in the x-axis direction (in the roll direction), in the y-axis direction (in the pitch direction), and in the z-axis direction (in the yaw direction).

The two legs 110R and 110L respectively include hip joint units, knee joint units and ankle joint units. The hip joint units of the two legs 110R and 110L respectively include rotary joints 16R and 16L in the roll direction, rotary joints 17R and 17L in the pitch direction, and rotary joints 18R and 18L in the yaw direction, thereby being rotatable in the x-axis direction (in the roll direction), in the y-axis direction (in the pitch direction), and in the z-axis direction (in the yaw direction). The knee joint units of the two legs 110R and 110L respectively include rotary joints 19R and 19L in the pitch direction, thereby being rotatable in the y-axis direction (in the pitch direction). The ankle joint units of the two legs 110R and 110L respectively include rotary joints 20R and 20L in the roll direction and rotary joints 21R and 21L in the pitch direction, thereby being rotatable in the x-axis direction (in the roll direction) and in the y-axis direction (in the pitch direction). FIG. 2 also shows feet 22R and 22L.

Respective degrees of freedom of the above-described vital sign measurement humanoid robot 100 are substantially achieved using respective actuators. In consideration of requirements, such as similarity to a natural shape of a human by excluding extra expansion in external appearance and pose control of an unstable structure, the actuators may be both small and lightweight.

Figure 3:
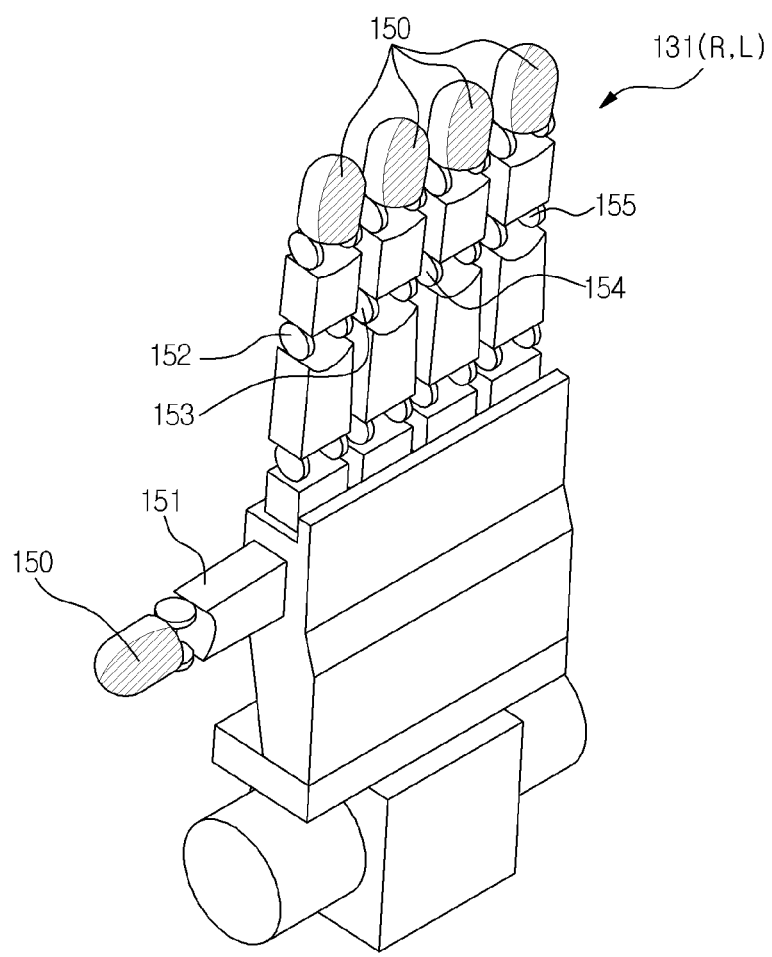
FIG. 3 is a view illustrating attachment of electrodes for vital sign measurement to a hand of the vital sign measurement robot in accordance with an embodiment.
Figure 4:
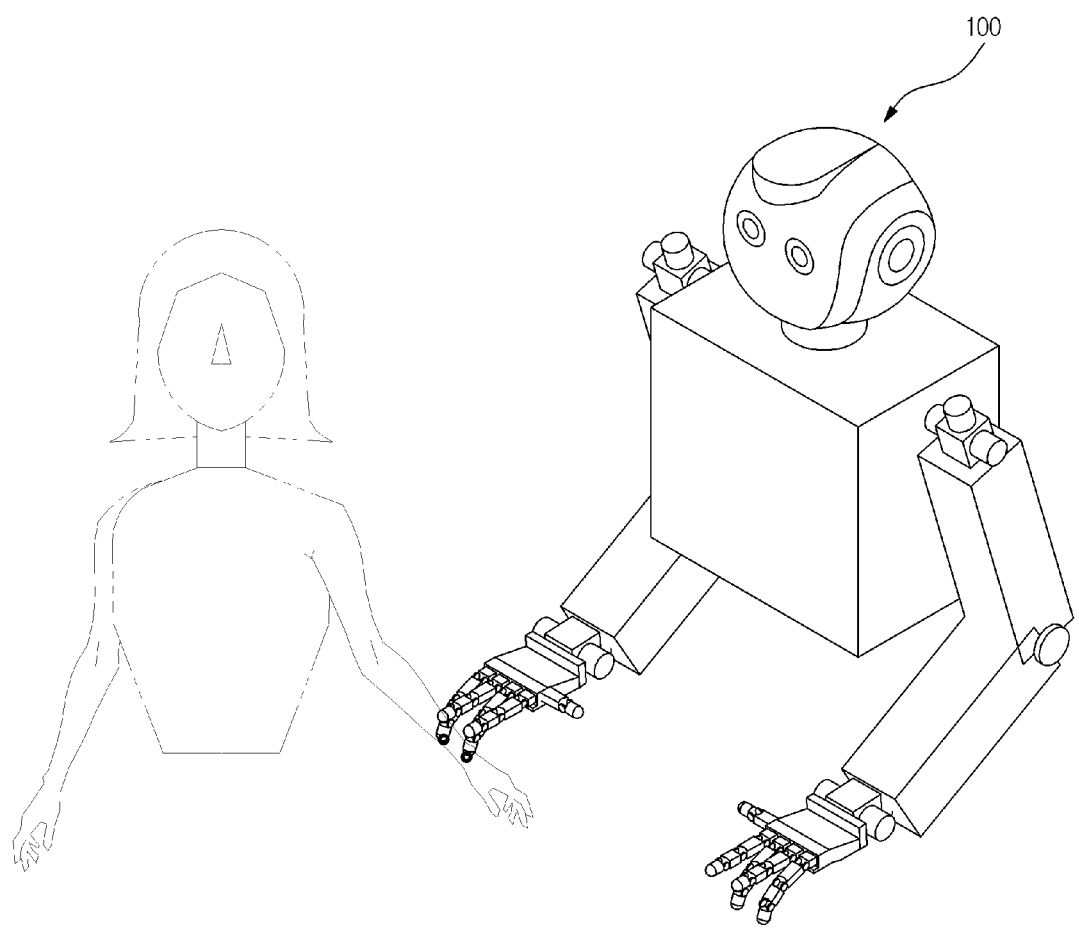
FIG. 4 is a view illustrating measurement of an electromyogram (EMG) measured by the vital sign measurement robot.
Figure 5:
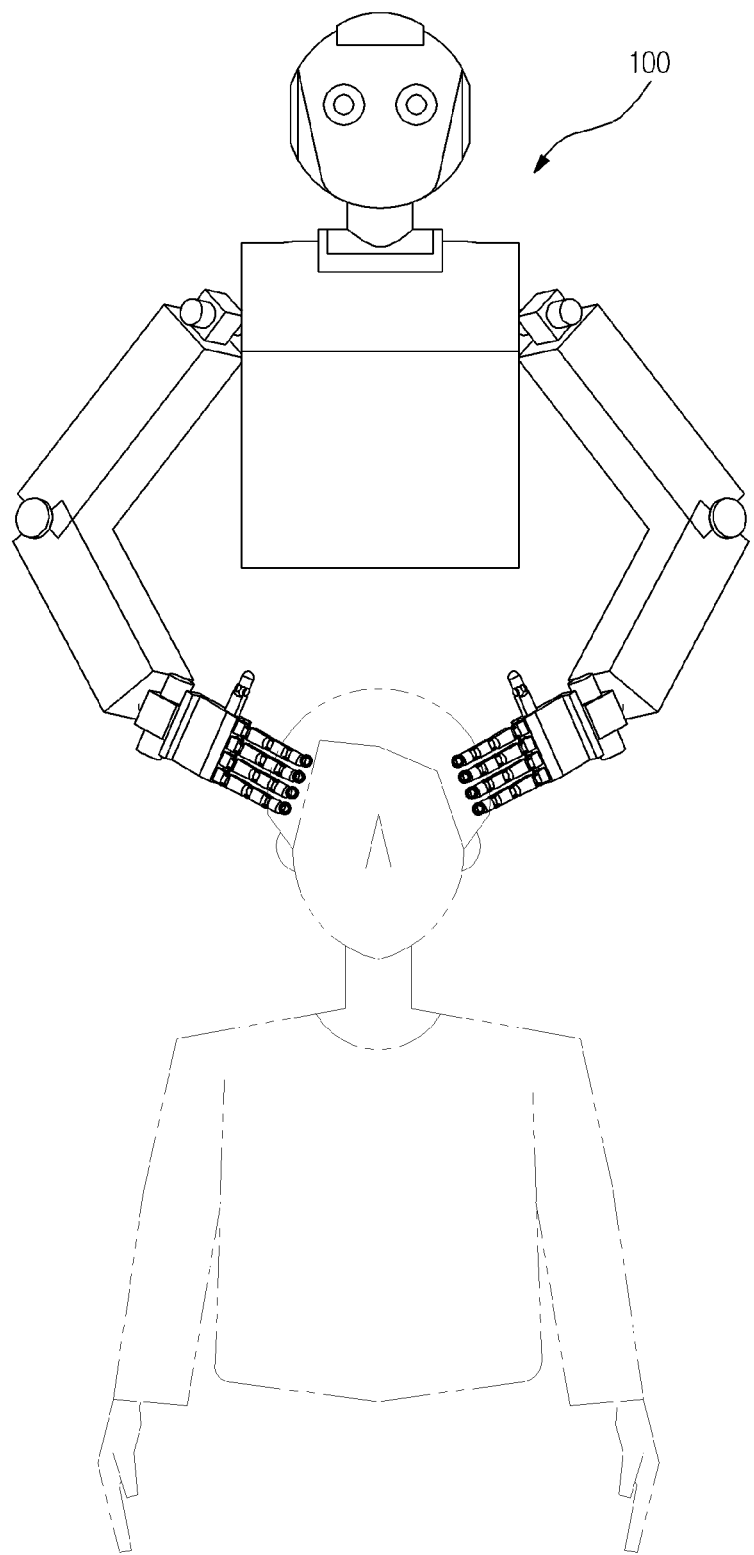
FIG. 5 is a view illustrating an electroencephalogram (EEG) measured by the vital sign measurement robot.

FIG. 3 is a view illustrating attachment of electrodes for vital sign measurement to the hand of the vital sign measurement robot in accordance with an embodiment, FIG. 4 is a view illustrating measurement of an electromyogram (EMG) measured by the vital sign measurement robot, and FIG. 5 is a view illustrating an electroencephalogram (EEG) measured by the vital sign measurement robot. Here, vital signs include all signs generated from a human body, such as an electromyogram (EMG), an electrocardiogram (EKG), am electroencephalogram (EEG) and so on.

One or more fingers 151 to 155 are provided on each of the hands 131R and 131L of the vital sign measurement robot 100. An electrode 150 is provided at the tip of each of the fingers 151 to 155 of the hands 131R and 131L. FIG. 3 illustrates that the electrode 150 is attached to the tip of each of the fingers 151 to 155. The electrodes 150 may be provided at both hands 131R and 131L or be provided at one of the hands 131R and 131L of the vital sign measurement robot 100. With reference to FIG. 4, the vital sign measurement robot 100 uses the plural electrodes 150 of one of the hands 131R and 131L during measurement of an EMG. With reference to FIG. 5, the vital sign measurement robot 100 uses the plural electrodes 150 of both hands 131R and 131L during measurement of an EEG.

Although the above embodiment exemplarily describes the plural electrodes 150 as being attached to the two hands 131R and 131L of the vital sign measurement robot 100, the number of the hands 131R and 131L and the number of the electrodes 150 are not limited as long as electrodes are attached to manipulators provided on the robot 100.

Hereinafter, a vital sign measurement method of the vital sign measurement robot 100 will be described.

Figure 6:
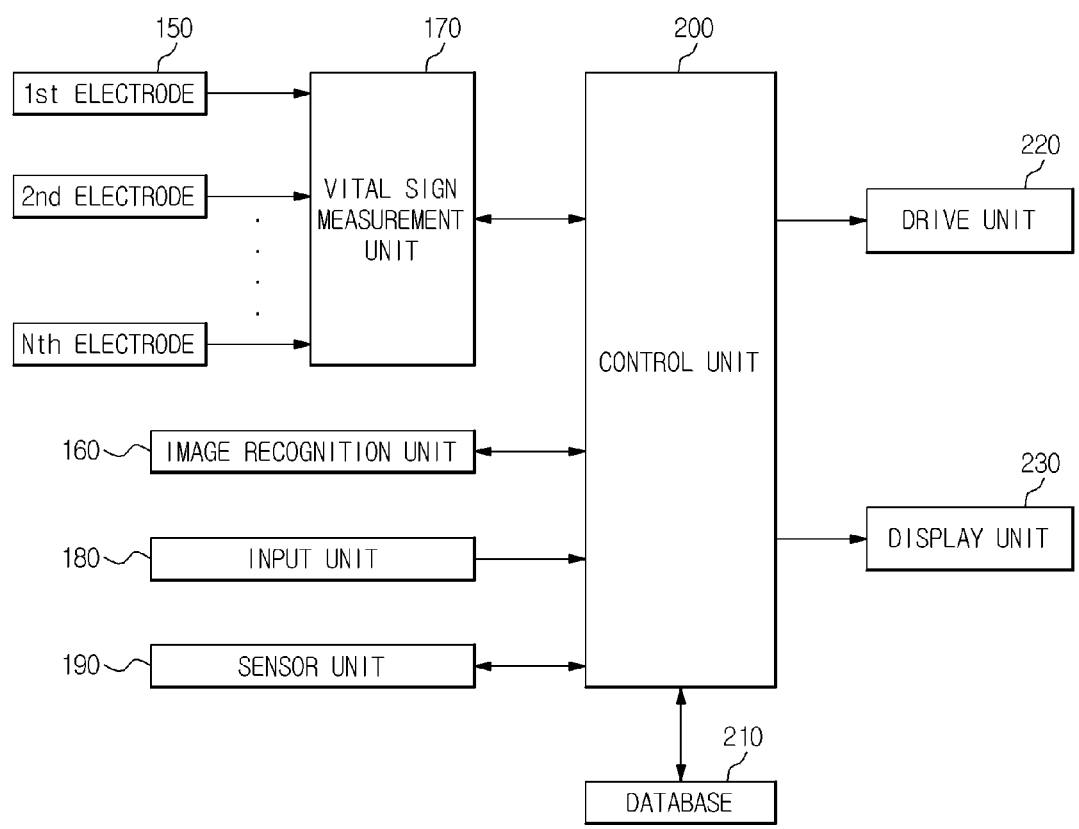
FIG. 6 is a control block diagram of the vital sign measurement robot in accordance with an embodiment.
Figure 7:
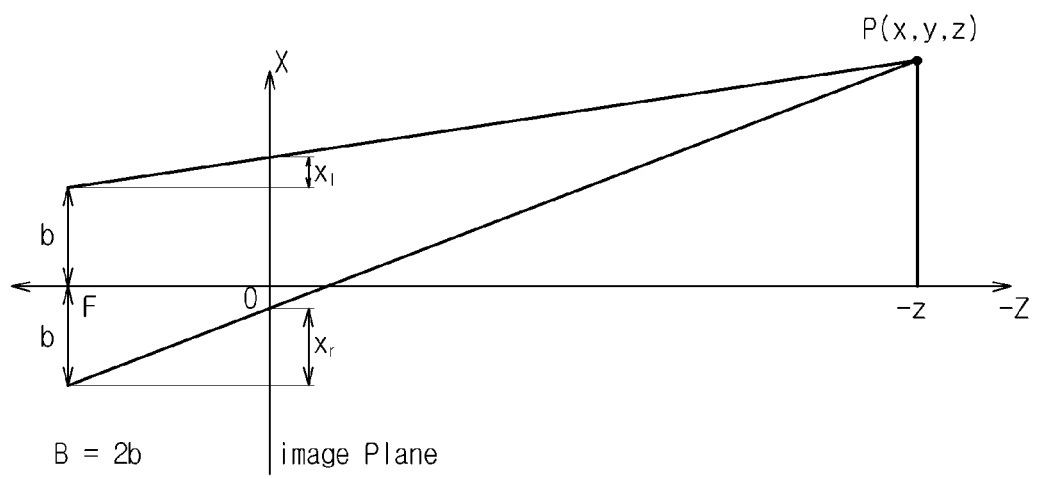
FIG. 7 is a graph illustrating the principle of a stereo vision system of the vital sign measurement robot in accordance with an embodiment.
Figure 8:
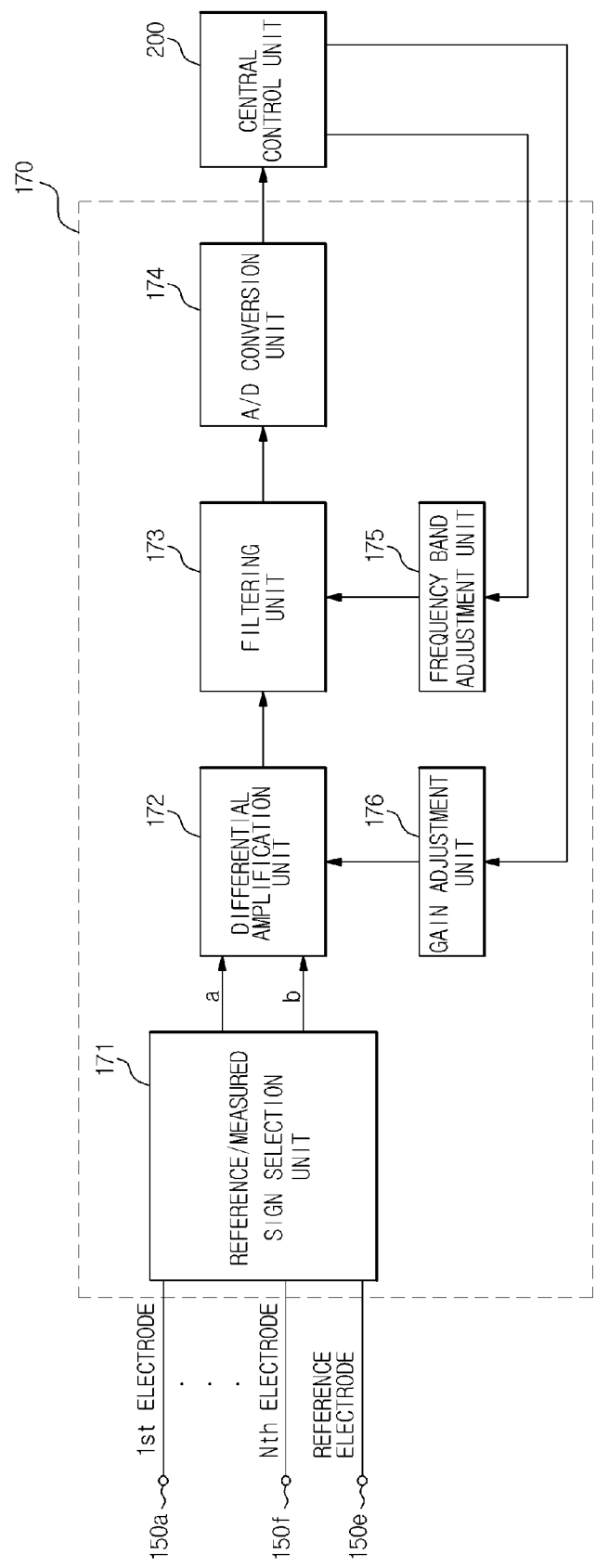
FIG. 8 is a detailed block diagram of a vital sign measurement unit of the vital sign measurement robot in accordance with an embodiment.

FIG. 6 is a control block diagram of the vital sign measurement robot in accordance with an embodiment, FIG. 7 is a graph illustrating the principle of a stereo vision system of the vital sign measurement robot in accordance with an embodiment, and FIG. 8 is a detailed block diagram of a vital sign measurement unit of the vital sign measurement robot in accordance with an embodiment.

The vital sign measurement robot 100 includes an image recognition unit 160, a vital sign measurement unit 170, an input unit 180, a sensor unit 190, a control unit 200, a database 210, a drive unit 220, and a display unit 230.

The image recognition unit 160 detects a distance between the vital sign measurement robot 100 and a person, vital signs of whom are to be measured, and a measurement portion of the body of the person. The image recognition unit 160 includes a device to three-dimensionally measure the person, the vital sings of whom are to be measured, such as a stereo vision system, a laser, or an infrared scanner. A method of three-dimensionally measuring the person using the stereo vision system, the laser, or the infrared scanner is well known. Therefore, by way of example, only operation and function of the stereo vision system will be briefly described.

The stereo vision system includes a plurality of CCD cameras serving as an image input device, and an image processing device to process image data received from the plurality of CCD cameras. The image processing device calculates movement data and stereo image processing data using the received images. The image processing device first calculates motion data based on the images obtained using the plurality of CCD cameras, and then obtains a stereo result using the motion value in stereo calculation.

The stereo vision system to measure the shape of a three-dimensional object generally employs two CCD cameras using the principle of human eyes. Hereinafter, the principle of the stereo vision system will be described with reference to FIG. 7. With reference to FIG. 7, 'F' represents a focal length of a lens, 'b' represents a distance from the central point of the lens to a halfway point (x=0) between the left and right CCD cameras, and 'B' represents a distance between the centers of the lenses of the left and right CCD cameras and is referred to as a base line. If an arbitrary point in a space is expressed as P(x, y, z), when the point P is projected on images of the left and right CCD cameras, values $X_l$ and $X_r$ are respectively displayed on left and right image planes and a difference $X_l-X_r$ between the values $X_l$ and $X_r$ is referred to as disparity.

The stereo vision system calculates three-dimensional data of an object. Here, the stereo vision system calculates a distance from the halfway point (x=0) between the left and right CCD cameras to the object, i.e., a value of a Z-axis component of the object, from the disparity value using triangulation, as described below.

$$z=F-(B*F)/d \qquad \text{Expression 1}$$

The vital sign measurement unit 170 detects various vital signs through the electrodes 150 contacting the skin of a user. Wet electrodes or dry electrodes may be used as the electrodes 150. The wet electrodes are disposable electrodes and the dry electrodes are made of a conductive polymer or a metal having high conductivity.

With reference to FIG. 8, the vital sign measurement unit 170 includes a reference/measured sign selection unit 171, a differential amplification unit 172, a filtering unit 173, an A/D conversion unit 174, a frequency band adjustment unit 175 and a gain adjustment unit 176.

The reference/measured sign selection unit 171 receives measured signs respectively supplied from a plurality of individual electrodes 150a to 150f and a reference sign supplied from a reference electrode 150e. The reference/measured sign selection unit 171 supplies one measured, which is sign sequentially selected from among the measured signs supplied from the plurality of individual electrodes 150a to 150f, and the reference sign supplied from the reference electrode 150e to a non-inverting input terminal a and an inverting terminal b of the differential amplification unit 172 under control of the control unit 200.

The differential amplification unit 172 differentially amplifies the measured sign supplied to the non-inverting input terminal a and the reference sign supplied to the inverting input terminal b.

The filtering unit 173 filters the differentially amplified sign supplied from the differential amplification unit 172, thereby removing power noise or movement noise.

The A/D conversion unit 174 converts the filtered sign supplied from the filtering unit 173 into a digital sign and then supplies the digital sign to the control unit 200.

The gain adjustment unit 176 adjusts a gain amplified by the differential amplification unit 172 under control of the control unit 200. The control unit 200 transfers the sign to the gain adjustment unit 176 so as to differentially adjust the gain according to the magnitude of the sign received from the A/D conversion unit 174 and to apply the proper gain according to the magnitude of a given vital sign.

The frequency band adjustment unit 175 adjusts the frequency band filtered by the filtering unit 173 under control of the control unit 200. The control unit 200 adjusts the frequency band to be filtered according to the type of the vital sign being measured. For example, in case of an EMG, the frequency band may be adjusted to 50 Hz-500 Hz, and in case of an EEG, the frequency band may be adjusted to 10 Hz-10,000 Hz. The reason for adjustment of the frequency band is to filter the sign band which is proper to be processed.

The input unit 180 receives vital sign measurement instructions from a user and then transfers the vital sign measurement instructions to the control unit 200.

The sensor unit 190 includes a pressure sensor to measure pressure of the electrodes 150 of the hands 131R and 131L applied to the skin or a speed sensor, such as a tachometer to calculate joint angles of manipulators. The control unit 200 calculates absolute coordinates of the respective joints from the calculated joint angles of the respective joints of the vital sign measurement robot 100. When the absolute coordinates of the respective joints are calculated, absolute positions of the respective joints and an absolute position of the vital sign measurement robot 100 are obtained.

When the control unit 200 receives the vital sign measurement instructions from the input unit 180, the control unit 200 receives a position of the vital sign measurement robot 100, a position of a person, and a measurement portion of the body of the person, from the image recognition unit 160.

When the control unit 200 receives the above predetermined data from the image recognition unit 160, the control unit 200 controls the drive unit 220 such that the electrodes of the hand(s) 131R and/or 131L are located at the measurement portion of the body of the person. The control unit 200 drives joints of the arms and the legs having plural degrees of freedom, thereby locating the electrodes 150 at the measurement portion of the body of the person.

After the electrodes 150 are located at the measurement portion of the body of the person, the control unit 200 may control the electrodes 150 to be pressed onto the measurement portion of the body of the person, at a predetermined pressure according to pressure data received through the pressure sensor. The control unit 200 locates the electrodes 150 at the measurement portion of the body of the person, while gradually increasing pressure applied to the measurement portion of the body of the person, and, upon confirming that the predetermined pressure is applied to the measurement portion of the body of the person, stops movement of the electrodes 150.

Alternatively, after the electrodes 150 are located at the measurement portion of the body of the person, the control unit 200 may control the electrodes 150 so as to be pressed onto the measurement portion of the body of the person, at a predetermined pressure through impedance control. The control unit 200 adjusts stiffness of finger tips through impedance control, thereby allowing the electrodes 150 to be precisely located on the skin of the person. Impedance control is a control method to overcome the limitations in position control having large stiffness (K; a stiffness coefficient in impedance characteristics) and to properly adjust stiffness so as to apply proper force to the fingers at which the electrodes 150 are located, and various stiffnesses may be applied between a target position and an actual position of the finger tip. Korean Patent Laid-open Publication No. 2010-0062653 discloses a finger control method of a robot using impedance control in detail.

When the electrodes 150 are precisely located at the measurement portion of the body of the person, through the above-described methods, the control unit 200 receives various vital signs measured by the vital sign measurement unit 170 through the electrodes 150 contacting the skin of the person. The control unit 200 analyzes the received vital signs, and displays a result of analysis through the display unit 230.

The database 210 stores positions of portions of the person, where vital signs are to be measured, according to types of the vital signs. For example, a portion of the person, where an EMG is to be measured, may be set to the wrist of the person, and a portion of the person, where an EEG is to be measured, may be the head of the person.

The drive unit 220 drives the joints under control of the control unit 200.

The display unit 230 displays vital signs to the outside such that a user may see the vital signs. The display unit 230 may provide a message or an alarm representing the result of analysis to the outside.

FIG. 9 is a flow chart illustrating a control method of a vital sign measurement robot in accordance with an embodiment.

The control unit 200 detects whether or not a user issues vital sign measurement instructions (operation 300), and detects a distance between the vital sign measurement robot 100 and a person, vital signs of whom are to be measured, and a measurement portion of the body of the person, upon detecting that the user has issued the vital sign measurement instructions (operation 310).

The distance between the vital sign measurement robot 100 and the person is detected through the image recognition unit 160, such as a stereo vision system or a laser. The image recognition unit 160 is configured to detect a three-dimensional shape of the person as well as to sense relative positions of the vital sign measurement robot 100 and the person. Further, the vital sign measurement robot 100 obtains joint angles of respective joints using a speed sensor, such as a tachometer, and calculates relative positions of the respective joints of the vital sign measurement robot 100 and the person by comparing absolute positions of the respective joints and an absolute position of the person, when the absolute positions of the joints are calculated from the respective joint angles.

The position of the vital sign measurement robot 100 means positions of the respective joints and hands of the vital sign measurement robot 100.

The measurement portion of the body of the person, the vital signs of whom are to be measured, is obtained by recognizing the three-dimensional shape of the person and then selecting corresponding data stored in advance in the database 210.

When the position of the vital sign measurement robot 100, the position of the person and the measurement portion of the body of the person are detected, the control unit 200 drives the manipulators so as to locate the electrodes 150 at the measurement portion of the body of the person (operation 320).

The control unit 200 controls the electrodes 150 so as to be pressed onto the measurement portion of the body of the person at a predetermined pressure. The pressing of the electrodes 150 onto the measurement portion of the body of the person is achieved using the above-described pressure sensor or through impedance control (operation 330).

The vital sign measurement unit 170 measures a vital sign, when the electrodes 150 are pressed onto the measurement portion of the body of the person at the predetermined pressure (operation 340).

The control unit 200 analyzes the vital sign transferred from the vital sign measurement unit 170, displays data, obtained through analysis, to the outside, and stores the data in the database (operation 350).

As is apparent from the above description, a vital sign measurement robot in accordance with an embodiment moves electrodes provided on hands to a person, vital signs of whom are to be measured, thereby measuring vital signs of the person.

The embodiments can be implemented in computing hardware and/or software, such as (in a non-limiting example) any computer that can store, retrieve, process and/or output data and/or communicate with other computers. For example, the control unit 200 in FIG. 6 can include a computer to perform calculations and/or operations described herein. A program/software implementing the embodiments may be recorded on non-transitory computer-readable media comprising computer-readable recording media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Therefore, in an embodiment, a robot hand has an electrode thereon. A computer detects a measurement portion of a body of a person having a vital sign to be measured, controls the robot hand so that the electrode is moved to thereby be located on the detected measurement portion of the body, and measures the vital sign via the electrode located at the measurement portion of the body.

Moreover, in an embodiment, a vital sign measurement robot includes an input unit to receive a vital sign measurement instruction; an image recognition unit to detect a distance between the vital sign measurement robot and a person having a vital sign to be measured, and a measurement portion of the body of the person, when the vital sign measurement instruction is received; a control unit to control a hand of the vital sign measurement robot to move an electrode provided on the hand so as to locate the electrode at the measurement portion of the body of the person, when the distance between the vital sign measurement robot and the person and the measurement portion of the body of the person are detected; and a vital sign measurement unit to measure the vital sign via the electrode, when the electrode is located at the measurement portion of the body of the person.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A vital sign measurement robot comprising:
   an input unit configured to receive a vital sign measurement instruction;
   an image recognition unit configured to detect a three-dimensional shape of a body of a person having a vital sign to be measured, to detect a distance between the vital sign measurement robot and the person, and to detect a measurement portion of the body of the person from the detected three-dimensional shape, when the vital sign measurement instruction is received;
   a control unit configured to control a hand of the vital sign measurement robot to move an electrode provided on the hand so as to locate the electrode at the measurement portion of the body of the person, in accordance with the distance between the vital sign measurement robot and the person and the measurement portion of the body of the person detected by the image recognition unit; and
   a vital sign measurement unit configured to measure the vital sign via the electrode, when the electrode is located at the measurement portion of the body of the person.

2. The vital sign measurement robot according to claim 1, further comprising:
   a pressure sensor configured to measure pressure applied by the electrode to the measurement portion of the body of the person,
   wherein, when the electrode is located at the measurement portion of the body of the person, the control unit controls the hand to cause the electrode to be pressed onto the measurement portion of the body of the person at a predetermined pressure according to data transferred from the pressure sensor.

3. The vital sign measurement robot according to claim 1, wherein, when the electrode is located at the measurement portion of the body of the person, the control unit controls the hand to cause the electrode to be pressed onto the measurement portion of the body of the person at a predetermined pressure through impedance control.

4. The vital sign measurement robot according to claim 1, further comprising:
   a tachometer configured to measure absolute positions of respective joints of the vital sign measurement robot, wherein
      the tachometer senses joint angles of the joints and transfers the joint angles to the control unit, and
      the control unit calculates absolute coordinates of the respective joints from the joint angles and controls the hand in accordance with the calculated absolute coordinates.

5. The vital sign measurement robot according to claim 1, further comprising:
   a display unit,
   wherein, the control unit receives data regarding the vital sign from the vital sign measurement unit, and outputs the received data through the display unit.

6. An apparatus comprising:
   a robot hand having an electrode thereon; and
   a computer configured for
      detecting a three-dimensional shape of a body of a person having a vital sign to be measured,
      detecting a measurement portion of the body of the person from the detected three-dimensional shape,
      controlling the robot hand so that the electrode is moved to thereby be located on the detected measurement portion of the body, and
      measuring the vital sign via the electrode located at the measurement portion of the body.

7. An apparatus according to claim 6, further comprising:
   a sensor configured for sensing pressure applied by the electrode to the body,
   wherein the computer controls the hand to control the applied pressure.

* * * * *